United States Patent
Edwards et al.

(10) Patent No.: US 6,598,458 B1
(45) Date of Patent: Jul. 29, 2003

(54) AUTOMATED SOIL GAS MONITORING CHAMBER

(75) Inventors: Nelson T. Edwards, Knoxville, TN (US); Jeffery S. Riggs, Lafollette, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 10/051,424

(22) Filed: Jan. 18, 2002

(51) Int. Cl.[7] .......................... G01N 33/18; G01N 1/10; E21B 47/00; E21B 11/02
(52) U.S. Cl. ...................... 73/19.1; 73/864.74; 166/264; 175/20
(58) Field of Search ................................ 73/19.1, 19.01, 73/152.25, 152.28, 864.52, 864.74; 166/264; 175/20

(56) References Cited

U.S. PATENT DOCUMENTS

| | | | |
|---|---|---|---|
| 4,618,855 A | 10/1986 | Harding et al. | 340/605 |
| 4,880,973 A | 11/1989 | Reynolds | |
| 5,355,739 A | 10/1994 | Cooper et al. | |
| 5,775,424 A | 7/1998 | Pemberton et al. | 166/264 |
| 5,889,217 A | 3/1999 | Rossabi et al. | 73/864.74 |
| 5,922,950 A | 7/1999 | Pemberton et al. | 73/152.28 |
| 2002/0000226 A1 | 1/2002 | Butnor et al. | 128/200 |
| 2002/0067953 A1 | 6/2002 | Ankeny et al. | 405/129.5 |

FOREIGN PATENT DOCUMENTS

DE          19852859          6/2000 ............ G01N/1/22

OTHER PUBLICATIONS

M. B. Rayment and P. G. Jarvis, "An Improved Open Chamber System for Measuring Soil CO2 Effluxes in the Field," Jl. of Geophysical Research, vol. 102 (No. D24), p. 28,779–784, (Dec. 26, 1997).
C. Fang and J. B. Moncrieff, "An Open–Top Chamber for Measuring Soil Respiration and the Influence of Pressure Difference on CO2 Efflux Measurement," Functional Ecology, vol. 12 No.), p. 319–325, (1998).

Primary Examiner—Hezron Williams
Assistant Examiner—J L Politzer
(74) Attorney, Agent, or Firm—Kirk A. Wilson

(57) ABSTRACT

A chamber for trapping soil gases as they evolve from the soil without disturbance to the soil and to the natural microclimate within the chamber has been invented. The chamber opens between measurements and therefore does not alter the metabolic processes that influence soil gas efflux rates. A multiple chamber system provides for repetitive multi-point sampling, undisturbed metabolic soil processes between sampling, and an essentially airtight sampling chamber operating at ambient pressure.

20 Claims, 3 Drawing Sheets

AUTOMATED SOIL GAS MONITORING CHAMBER

The United States Government has rights in this invention pursuant to contract number DE-AC05-00OR22725 between the United States Department of Energy and UT-Battelle, LLC.

BACKGROUND OF THE INVENTION

Gaseous effluxes from soil are indicators of biological processes that are occurring below ground and if quantified the relative importance of particular processes to the whole ecosystem can be determined. For example, the efflux of $CO_2$ out of soil, commonly referred to as soil respiration, comprises the respiration of plant roots and the respiration of soil heterotrophs (bacteria, fungi, arthropods). Soil respiration is a very large fraction of gross primary productivity, and its quantification is a high priority in attempts to establish ecosystem carbon budgets. The current emphasis on ecosystem management for increased carbon sequestration mandates improved monitoring of soil respiration. If the carbon flux from the soil cannot be accurately measured, it cannot be assumed that there is increased storage of carbon in long-term soil pools. The importance of quantifying rates of $CO_2$ efflux from soils was recently accentuated by the European Science Foundation's workshop this summer that addressed the problems associated with measurements of soil respiration.

The primary problem facing strategies for measurement of soil respiration is the tremendous spatial and temporal heterogeneity in the rates of soil $CO_2$ efflux. $CO_2$ efflux varies seasonally and over the course of a day, mostly in response to root growth phenology and to changing temperature. Currently, this variation is handled by establishing temperature response relationships that can be applied to point-in-time measurements of efflux and continuously monitored soil temperature. The correction factor can be so large, however, that this approach may introduce errors. This is further exacerbated by the inability to accurately assess the phenology and magnitude of root growth below ground. Spatial heterogeneity in soil $CO_2$ efflux can be handled by making many replicate measurements, but because each measurement takes some time, the spatial variation becomes confounded with temporal variation. Most of these same problems face researchers who attempt to measure efflux of other greenhouse gases, such as $CH_4$, $N_2O$, $N_2$, and $NO_2$. Instrumentation currently available for continuously measuring soil gas efflux do not solve these problems because techniques used for trapping the gases alter the microclimate of the soil and therefore alter the rates of gas efflux. The chamber in this invention used in conjunction with automated switching and analysis can solve the problems associated with temporal variability.

U.S. Pat. No. 5,355,739 to Cooper et al. is representative of sampling chambers that prevent natural metabolic processes and thus influence soil gas efflux rates. This point-in-time measuring device, especially designed for spot measurements of gas emissions, is not suitable for continuously monitoring gas emissions from soil or even from landfills because it does not permit the natural drying and wetting of the soil or landfill when left in place over long time periods.

The criteria for perfecting an automated soil gas efflux system with the capability to monitor rates continuously over long time periods revolve primarily around the development of an appropriate chamber for trapping the gases as they evolve from the soil without disturbance to the soil and to the natural microclimate within the chamber. The gases evolving from the soil must be moved with the ambient air stream at constant and quantifiable flow rates sequentially through many such chambers inverted over the soil surface to an appropriate analysis system. The analysis system must accurately monitor concentration differences of the gases in the air before entering (reference air) and after exiting the chambers (sample air). Furthermore, the air moving through the chamber should not disturb the natural air boundary layer at the soil surface more than might occur at average wind speeds. The air stream should not alter the atmospheric pressure within the chamber.

Continuous observations of soil gas efflux when sustained over a range of environmental and growth conditions allow for the quantification of component processes contributing to whole ecosystem soil gas flux. Instrumentation currently available for continuously measuring soil gas efflux do not solve these problems because techniques used for trapping the gases alter the microclimate of the soil and therefore alter the rates of gas efflux.

BRIEF SUMMARY OF THE INVENTION

A chamber for trapping soil gases as they evolve from the soil without disturbance to the soil and to the natural microclimate within the chamber has been invented. The chamber does not alter the metabolic processes that influence soil gas efflux rates. A multiple chamber system provides for repetitive multi-point sampling, undisturbed metabolic soil processes between sampling, and an essentially airtight seal around the chamber housing during sampling. The chamber housing operates at essentially ambient atmospheric pressure during sampling.

The chamber operates by closing over the soil in response to a computer signal and remains closed for a preselected time period, preferably a 14 minute period, before opening again. By being closed only periodically, the chamber allows normal drying and wetting of the soil between measurements. After testing a single prototype chamber, seven additional chambers were built and an automated switching system was purchased and programed to sequentially open and close the chambers in concert with an automated infrared gas analysis system. Soil respiration rates measured with the automated chambers were in agreement with proven point-in-time measurements and have been run for several months without altering the soil microclimate.

DETAILED DESCRIPTION OF THE INVENTION

Figure 1:
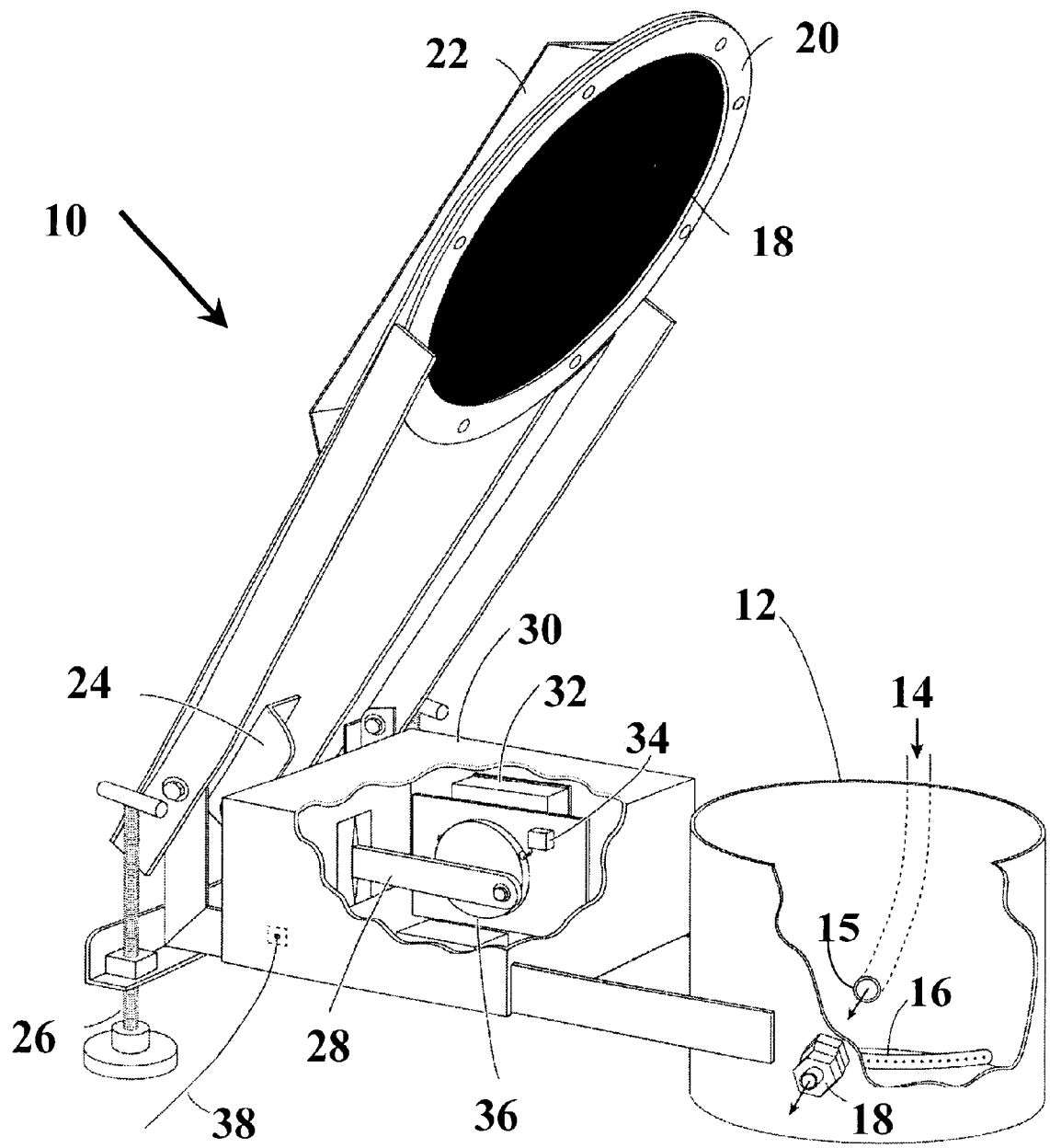
FIG. 1 illustrates a single chamber and its components.
Figure 2:
FIG. 2 is a photograph showing one of the automated chambers in the open position.
Figure 3:
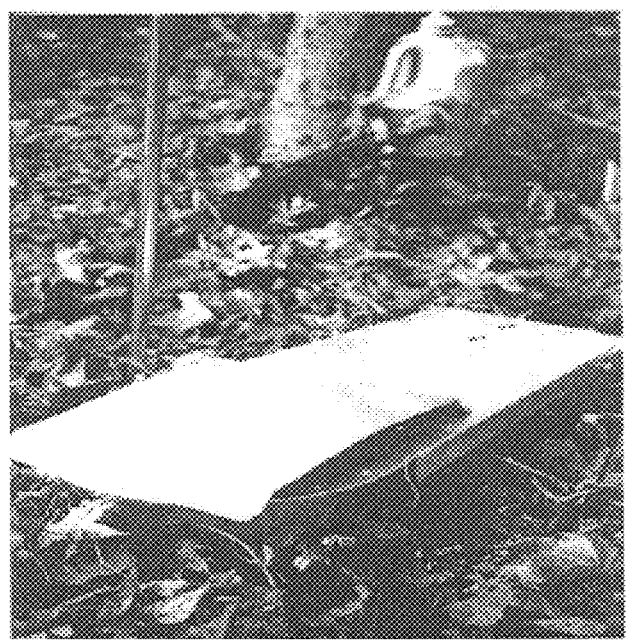
FIG. 3 is a photograph showing one of the automated chambers in the closed position.

The chamber 10 shown in FIG. 1 comprises a metal cylinder chamber housing 12 (20 cm diameter×15 cm depth) open on both ends, a hinged neoprene cover 18 for the chamber housing, and a means for periodically removing the hinged neoprene cover 18. The means for periodically removing the cover 18 comprises a motor operating lifting device further comprising a small electric motor 32 periodically rotating a disc 36 on the motor shaft, a push rod 28 pinned to the disc for cranking the lid open and closed, and a switch 34 which is remotely activated via an automated switching system (not shown) to turn-on the motor. The bottom of the cylinder is sharp so that it can be pushed into the soil to form an essentaily airtight seal with the soil. When closed the elastic neoprene lid 18 stretches tightly over the top of the cylinder forming an essentially airtight chamber for trapping gases diffusing from the soil. An electric pump (not shown) pulls air through a 0.5 cm diameter plastic tube (sample line) via the exhaust port 18 from the chamber to an infrared gas analyzer (IRGA) (not shown). The tubing is connected to a manifold 16 mounted inside the chamber about 5 cm above the soil surface. The manifold 16, which serves as an air mixer, is protected from rainfall by a small metal roof (not shown) when the chamber is in the open position. Air enters the chamber through an intake port 15, approximately 2.5 cm in diameter, on the opposite side from the manifold. A plastic tube 14, approximately 2.5 cm in diameter, connects from this port to a mixing bottle (not shown) approximately 18 liters. Air is also pumped through plastic tube (reference line), approximately 0.5 cm in diameter, from the mixing bottle directly to the IRGA, by-passing the soil chamber.

Sample specifications and materials used for construction of the preferred chamber include:

1) Chamber housing and framing; heat-treated aluminum (60–61 T6), about 3 mm thick
2) Legs 26 of stainless steel (16 cm tall)
3) Rubber cover 18—2 mm thick neoprene
4) Heat shield 22—aluminum sheeting—enough to shade neoprene lid
5) Overall length of hinged lid—60 cm
6) Chamber housing 12—19.5 cm ID, 15 cm deep pipe— about 2 mm thick
7) Base framework connected to chamber—41 cm long
8) Framework width (where legs attach)—35 cm
9) Exhaust tubing—4 mm ID
10) Intake tubing 14—3.5 cm ID
11) Adjustable push rod attachment 24—9 cm long
12) Disc 36 attached to shaft of motor 32—6.4 cm diameter
13) Push rod 28—9 mm thick, 2 cm wide, 20 cm long
14) Motor 32—1 rpm AC gear motor 1/400 hp, 50 in-lbs, 115 volts AC 60 HZ (Grainger part #2z804)
15) Switch 34—SPDT with roller lever (Radio Shack part #275-017)
16) Solid state relay (not shown)—Crydom Model 1202, 3-32 DC volt range—control input, 120 volts AC output.

The chamber operates by closing over the soil in response to a computer signal 38 and remains closed for a pre-set time interval before opening again. By being closed only periodically, the chamber allows normal drying and wetting of the soil between measurements. After testing a single prototype chamber, seven additional chambers were built and an automated switching system was purchased and programed to sequentially open and close the chambers in concert with IRGA system. The switching system would allow for an additional 24 chambers if needed. Two mass flow controllers (not shown) located on the pump-side of the IRGA maintains equal airflow rates (1 liter per minute) through the sample line and the reference line. An existing automated IRGA system, currently used for measuring stem respiration was used for testing the soil chambers. During operation two of the eight chambers are closed while the other six are open. Each chamber remains closed for 14 minutes and $CO_2$ concentrations are recorded during only the last two minutes. Carbon dioxide concentrations in the sample line and reference line are measured with the IRGA operating in differential mode (i.e. concentration values are recorded as a change in $CO_2$ concentrations).

Figure 4:
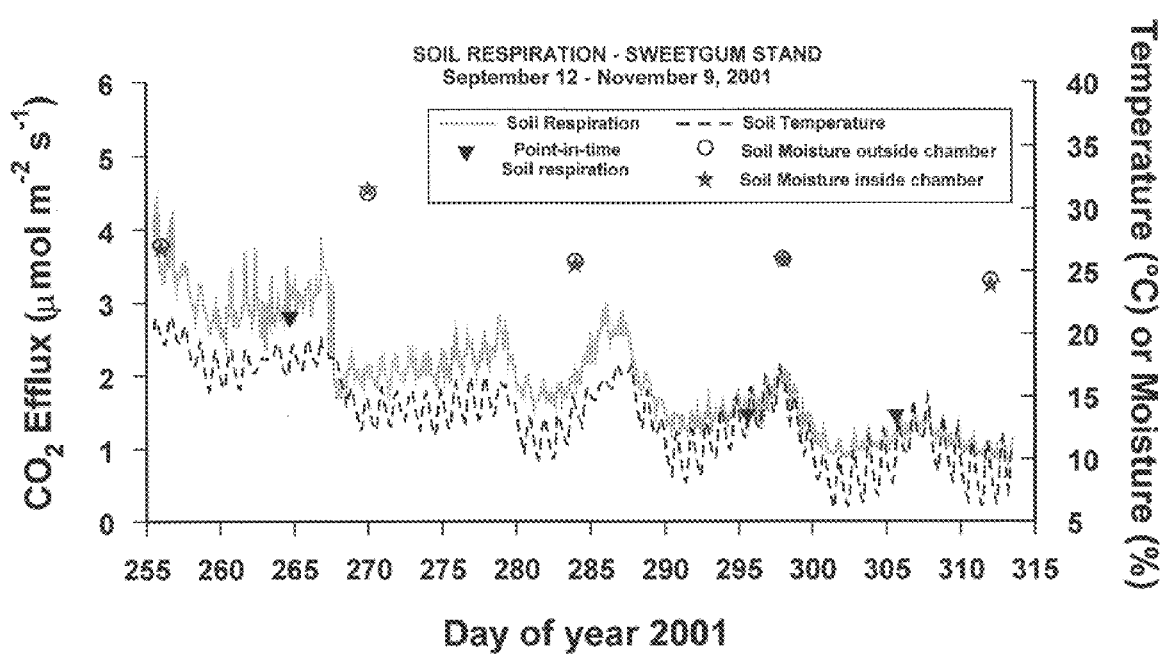
FIG. 4 is a graph showing soil respiration and temperature measurements taken during two months in the forest floor of a sweet gum stand.

Initial tests revealed that air temperatures inside the chamber increased slightly during the 14 minutes after closing. This was corrected by constructing a reflective roof heat shield 22 over the neoprene roof. At night the closed lid tends to trap heat from the soil resulting in about a 1° C. increased in air temperature during the 14-minute period. However, there was no detectable change in soil temperature (FIG. 4). Increasing flow rates could potentially eliminate all temperature increases, but flow rates exceeding normal wind speed can result in increased diffusion of gases from the soil. $CO_2$ efflux rates were tested at flow rates in the range of 0.5 to 1 liters per minute, representative of a normal range of wind speeds in the region, and could not detect differences in efflux rates.

Pressure gradients between the outside atmosphere and inside the chamber can have large effects on rates of gaseous efflux from soil, especially when air is being pulled (or sucked) through the chamber as in this system. If the opening on the intake side of our chamber was 2.25 times greater in area than the exhaust side, a small negative pressure occurred in the chamber resulting in $CO_2$ efflux rates 4 times greater than expected. Increasing the intake opening to an area nearly 15 times greater than the exhaust opening prevented the pressure gradient and eliminated the abnormally high $CO_2$ efflux rates. In fact, restricting the size of the opening on the mixing bottle results in negative pressure in the soil chamber. Using this technique we were able to demonstrate the air tightness of the system.

Soil respiration rates measured with the automated chamber were in agreement with proven point-in-time measurements (FIG. 4) and have been run for several weeks without altering the soil microclimate.

What is claimed is:

1. A soil gas monitoring device comprising;
    a) a chamber having an elongated chamber housing with an upper open end and a lower open end; said lower open end removably coupled essentially airtight to the soil,
    b) a cover removably coupled using an essentially airtight elastic seal to said upper open end thereby forming a closed chamber,
    c) an intake port in said chamber housing,
    d) an exhaust port in said chamber housing,
    e) an exhaust manifold disposed in said chamber and removably connected to said exhaust port,
    f) a means for open circuit sampling said closed chamber for efflux gases during a selectable monitoring time via said exhaust manifold, said selectable monitoring time having a selectable recording time,
    g) a means for periodically removing said essentially airtight cover thereby exposing said chamber to ambient conditions, and
    h) a heat shield removably disposed on said cover.

2. The soil gas monitoring device of claim 1 wherein said efflux gases are selected from the group consisting of $CH_4$, $N_2O$, $N_2$, $CH_3$, $NO_2$, and $NO_4$.

3. The soil gas monitoring device of claim 1 wherein said soil maintains undisturbed metabolic processes between sampling.

4. The soil gas monitoring device of claim 1 wherein the area of said intake port is between about 2.25 and 15 times greater than the area of said exhaust port, preferably about 15 times greater.

5. The soil gas monitoring device of claim 1 wherein said means for sampling comprises an infrared gas analyzer.

6. The soil gas monitoring device of claim 1 wherein said means for periodically removing said essentially airtight cover comprises a motor operated lifting device.

7. A soil gas monitoring system comprising;
 a) at least one soil gas monitoring device further comprising;
   1) a chamber having an elongated chamber housing with an upper open end and a lower open end; said lower open end removably coupled essentially airtight to the soil,
   2) a cover removably coupled using an essentially airtight elastic seal to said upper open end thereby forming a closed chamber,
   3) an intake port in said chamber housing,
   4) an exhaust port in said chamber housing,
   5) an exhaust manifold disposed in said chamber and removably connected to said exhaust port,
   6) a means for open circuit sampling said closed chamber for efflux gases during a selectable monitoring time via said exhaust manifold, said selectable monitoring time having a selectable recording time,
   7) a means for periodically removing said essentially airtight cover thereby exposing said chamber to ambient conditions,
   8) a heat shield removably disposed on said cover, and
 b) a means for controlling said at least one soil gas monitoring device for repetitive multi-point sampling.

8. The soil gas monitoring system of claim 7 wherein said efflux gases are selected from Fe group consisting of $CH_4$, $N_2O$, $N_2$, and $NO_2$.

9. The soil gas monitoring system of claim 7 wherein said soil maintains undisturbed metabolic processes between sampling.

10. The soil gas monitoring system of claim 7 wherein the area of said intake port is between about 2.25 and 15 times greater than the area of said exhaust port, preferably about 15 times greater.

11. The soil gas monitoring system of claim 7 wherein said means for sampling comprises an infrared gas analyzer.

12. The soil gas monitoring system of claim 7 wherein said means for periodically removing said essentially airtight cover comprises a motor operated lifting device.

13. The soil gas monitoring system of claim 7 wherein said means for controlling comprises a computer controlled automated switching system.

14. A method for monitoring soil gas efflux comprising;
 a) stationing at least one open soil gas monitoring device onto soil in a sampling area, said monitoring device having a removably disposed heat shield,
 b) closing said at least one gas monitoring device periodically,
 c) pulling an air sample from the closed chamber of said soil gas monitoring device,
 d) analyzing said air sample for efflux gases,
 e) repeating steps b) through d) for each soil gas monitoring device using a computer controlled automated switching system.

15. The method of claim 14 wherein said efflux gases are selected from the group consisting of $CH_4$, $N_2O$, $N_2$, $NO_2$.

16. The method of claim 14 wherein said soil maintains undisturbed metabolic processes between sampling.

17. The method of claim 14 wherein said pulling of air sample is performed at ambient atmospheric pressure.

18. The method of claim 14 wherein said analyzing step comprises an infrared gas analyzer.

19. The method of claim 14 wherein said closing step time period is about fourteen minutes.

20. The method of claim 19 wherein said pulling step time period is about the last two minutes of the said fourteen minute closing period.

\* \* \* \* \*